(12) United States Patent
Liu et al.

(10) Patent No.: US 11,680,035 B2
(45) Date of Patent: Jun. 20, 2023

(54) HOLE TRANSPORT MATERIAL, SYNTHESIS THEREOF, AND SOLAR CELL

(71) Applicant: Ecole Polytechnique Federale de Lausanne (EPFL), Lausanne (CH)

(72) Inventors: Yuhang Liu, Bussigny-Lausanne (CH); Shaik Mohammed Zakeeruddin, Bussigny-Lausanne (CH); Michael Graetzel, St-Sulpice (CH); Michael Bauer, Ulm (DE); Peter Bäuerle, Elchingen (DE)

(73) Assignee: Ecole Polytechnique Federale de Lausanne (EPFL), Lausanne (CH)

( * ) Notice: Subject to any disclaimer, the term of this patent is extended or adjusted under 35 U.S.C. 154(b) by 136 days.

(21) Appl. No.: 17/391,140

(22) Filed: Aug. 2, 2021

(65) Prior Publication Data

US 2022/0033342 A1 Feb. 3, 2022

(30) Foreign Application Priority Data

Aug. 3, 2020 (EP) .................................... 20189226

(51) Int. Cl.
| | |
|---|---|
| *C07C 211/54* | (2006.01) |
| *H01L 51/00* | (2006.01) |
| *H10K 30/10* | (2023.01) |
| *H10K 85/60* | (2023.01) |
| *H10K 50/155* | (2023.01) |

(52) U.S. Cl.
CPC ............ *C07C 211/54* (2013.01); *H10K 30/10* (2023.02); *H10K 85/631* (2023.02); *C07C 2601/16* (2017.05); *H10K 50/155* (2023.02)

(58) Field of Classification Search
CPC .............. C07C 211/54; H01L 51/0059; H01L 51/4213
See application file for complete search history.

(56) References Cited

U.S. PATENT DOCUMENTS

| | | | | | |
|---|---|---|---|---|---|
| 5,681,664 A | * | 10/1997 | Tamano | ............... | G03G 5/0618 428/917 |
| 5,948,941 A | * | 9/1999 | Tamano | ................ | C07C 215/82 430/73 |
| 6,541,129 B1 | * | 4/2003 | Kawamura | ........... | C07C 211/58 564/429 |

OTHER PUBLICATIONS

Extended European Search Report; European Patent Office; Application No. 20189226.2; dated Jan. 27, 2021; 5 pages.
Dong Shi et al.; Spiro-OMeTAD Single Crystals: Remarkably Enhanced Charge-Carrier Transport via Mesoscale Ordering; Science Advances; Apr. 15, 2016; 7 pages; vol. 2, No. 4.

* cited by examiner

*Primary Examiner* — Sikarl A Witherspoon
(74) *Attorney, Agent, or Firm* — Taft Stettinius & Hollister LLP

(57) ABSTRACT

The organic small molecule 4,4',4",4'''-(5,5-dimethoxycyclopenta-1,3-diene-1,2,3,4-tetrayl)tetrakis(N,N-bis(4-methoxyhenyl)aniline (CPDA 1), shows electrochemical properties very close to spiro-OMeTAD indicating a high compatibility with PSC systems for its use as a hole transport material (HTM). The implementation of the cyclopentadiene dimethyl acetale core helps to red shift the absorption onset of the films as well as provide a flexible spatial configuration of the molecule, which is essential for optimum film forming properties. Transient and steady state emission analysis as well as hole mobility measurements indicate that the new HTM allows a better charge extraction, transport and separation than the spiro-OMeTAD reference compound. PSCs based on the new CPDA 1 show a PCE close to 23% with lower hysteresis than its analogue. Stability studies performed under ambient, heated and humid conditions all showed that CPDA 1 is over-performing spiro-OMeTAD. Furthermore the production cost of CPDA 1 is about 10 times lower than that of spiro-OMeTAD, contributing to render PSCs more affordable.

13 Claims, 8 Drawing Sheets

CPDA 1

Spiro-OMeTAD

HOLE TRANSPORT MATERIAL, SYNTHESIS THEREOF, AND SOLAR CELL

CROSS REFERENCE TO RELATED APPLICATIONS

This application claims priority to European Patent Application No. 20189226.2 filed Aug. 3, 2020, the contents of which are hereby incorporated by reference in their entirety.

FIELD OF THE INVENTION

The field of the invention relates to hole transport materials (HTMs) and their use in perovskite based solar cells (PSCs).

More particularly the invention relates to a molecule having a structure comprising a core flanked by four arylamine moieties, its synthesis, and the use of said compound in an HTM layer of a PSC. The invention relates also to a PSC, specifically a hybrid metal halide perovskite based solar cell, incorporating such an HTM.

BACKGROUND AND RELATED PRIOR ART

Hybrid metal halide perovskite materials have been successfully used as light absorbing layer in solar cells due to their facile preparation process as well as their excellent optoelectronic properties[1]. The power conversion efficiency (PCE) of perovskite solar cells (PSCs) reached about 23-25% during the past few years[2]. Hole transporting materials (HTMs) are critically important for high performance of the PSCs to construct effective hole-extraction and electron blocking layer[3]. Besides high hole-mobility and well aligned energy levels, the production cost is also becoming more important for HTMs now that the field of PSCs is moving from the academia to industrial commercialization[4]. Organic small molecule HTMs have been widely studied due to their advantages of a well-defined chemical structure[5], tunable energy levels for different perovskite active materials[6], and good batch-to batch reproducibilityn. Spiro-OMeTAD was the most widely used small molecule HTM exhibiting power conversion efficiencies (PCE) exceeding 24%[8]. However, those performances came with the cost of a difficult synthesis of the Spiro-OMeTAD molecule because of its 9,9'-spirobifluorene core (Spiro)[9], together with poor operational stability that is accompanied with lowered glass-transition temperature ($T_g$) upon introducing dopants[10]. Considerable means and efforts were invested into developing low cost and synthetically accessible cores for hole transporting materials that would yield stable and highly efficient devices when incorporated into PSC[11], While none deliver better photovoltaic performance as compared to Spiro based HTMs with PCE>23%. For such a reason, the developments of novel HTMs surpassing spiro-OMeTAD in PSC in terms of i) efficiency, ii) long-term stability under thermal and light stress, iii) high glass transition temperature upon doping and iv) low-cost is an important objective.

SUMMARY OF THE INVENTION

The invention is made in view of the aforementioned problems and drawbacks in the related art.

In its broadest sense, the invention provides a compound having a structure comprising a substituted cyclopentadiene core flanked by four arylamine based moieties, having one of formulas (I) and (II)

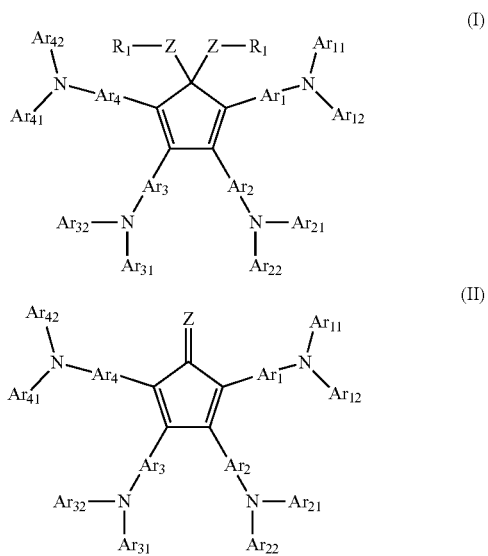

wherein Z=CH$_2$—, or O or S or Se,
wherein R$_1$ is selected from C1-C20 linear or branched alkyl chains or alkoxy chains of formula

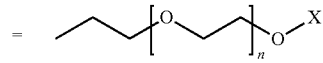

Where X=(CH$_2$)$_n$NR$_x{}^{3+}$M$^-$; PR$_x{}^{3+}$M$^-$; SO$_3$R$_x$.

Where R$_x$ is selected from C1-C20 linear or branched alkyl chains.

Where M$^-$ represents a counterion. Examples of counterions M$^-$ are: F$^-$, I$^-$, Br$^-$, Cl$^-$, [N(CN)$_2$]$^-$, [N(SO$_2$CF$_3$)$_2$]$^-$, [PF$_6$]$^-$, [BF$_4$]$^-$, [NO$_3$]$^-$, [C(CN)$_3$]$^-$, [B(CN)$_4$]$^-$, [CF$_3$COO]$^-$, [ClO$_4$]$^-$ Where n=0 to 20.

wherein Ar$_1$, Ar$_2$, Ar$_3$ and Ar$_4$ are identical or different moieties selected from aromatic or heteroaromatic ring systems having one or more aromatic rings comprising 5 to 40 ring atoms and one or more of the atoms independently selected from C, N, O, S, Se, and groups, SiR'$_2$, or NR'; wherein R' is selected from C1-C20 alkyl, C2-C20 alkenyl, C2-C20 alkynyl, C4-C20 unsubstituted and substituted aryl, and C1-C20 fluoroalkyl group, wherein said alkyl, alkenyl, alkynyl, and fluoroalkyl, if they comprise 3 or more carbons may be linear, branched or cyclic.

wherein the said one or more aromatic rings may further be substituted by one or more moieties independently selected from H, keto (=O) group, fluoro group, C1-C20 alkyl, C1-C20 alkoxy, C2-C20 alkenyl and C2-C20 alkynyl group.

According to an embodiment, Ar$_1$, Ar$_2$, Ar$_3$ or Ar$_4$ are identically or independently one from the other selected from the group consisting of

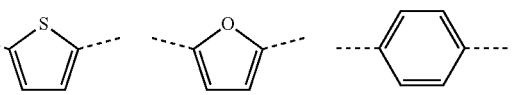

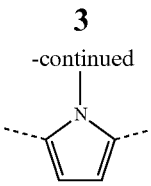

wherein $Ar_{n1}$—$Ar_{n2}$ (n=1, 2, 3, 4) are identical or different moieties selected from aromatic or heteroaromatic ring system having one or more aromatic rings comprising 5 to 40 ring atoms and one or more atoms, resp. groups, independently selected from C, N, O, S, Se, $CR'_2$, $SiR'_2$, or NR', wherein R' is selected from C1-C20 alkyl, C2-C20 alkenyl, C2-C20 alkynyl, C4-C20 aryl, and C1-C20 fluoroalkyl group, wherein said alkyl, alkenyl, alkynyl, and fluoroalkyl, if they comprise 3 or more carbons may be linear, branched or cyclic and wherein aryl group may be substituted;

wherein said aromatic ring may be further substituted by one or more moieties independently selected from H, keto (=O) group, fluoro group, C1-C20 alkyl, C1-C20 alkoxy, C2-C20 alkenyl and C2-C20 alkynyl group.

For example, $Ar_{n1}$—$Ar_{n2}$ (n=1, 2, 3, 4) are identically or independently one from the other selected from the group consisting of

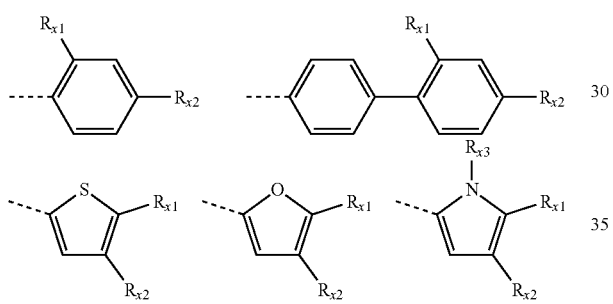

Where $R_{x1}$ or $R_{x2}$ are selected from —H, —$OR_{x3}$, —$SR_{x3}$, —$R_{x3}$;

Where $R_{x3}$ is selected from C1-C20 linear or branched alkyl chains or alkoxy chains.

Or, $Ar_{n1}$, $Ar_{n2}$ (n=1, 2, 3, 4)

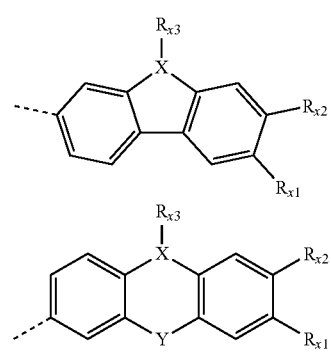

Where $R_{x1}$ or $R_{x2}$ are selected from —H, —$OR_{x3}$, —$SR_{x3}$, —$R_{x3}$ Where X=N or P, where Y=O or S.

Where $R_{x3}$ is selected from C1-C20 linear or branched alkyl chains, alkoxy chains.

Or, $Ar_{n1}$+$Ar_{n2}$ (n=1, 2, 3, 4)

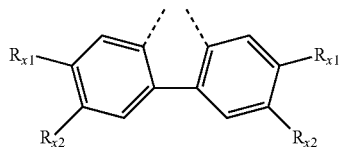

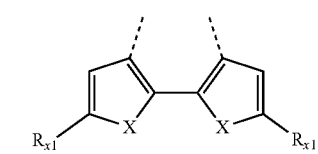

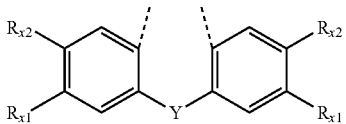

Where $R_{x1}$ or $R_{x2}$ are selected from —H, —$OR_{x3}$, —$SR_{x3}$, —$R_{x3}$ Where X=N or P, where Y=O or S.

Where $R_{x3}$ is selected from C1-C20 linear or branched alkyl chains, alkoxy chains.

Where the two dashed-lines are prone to represent C—N bond that is connected to the central N atom in the arylamine moietie structure, for example:

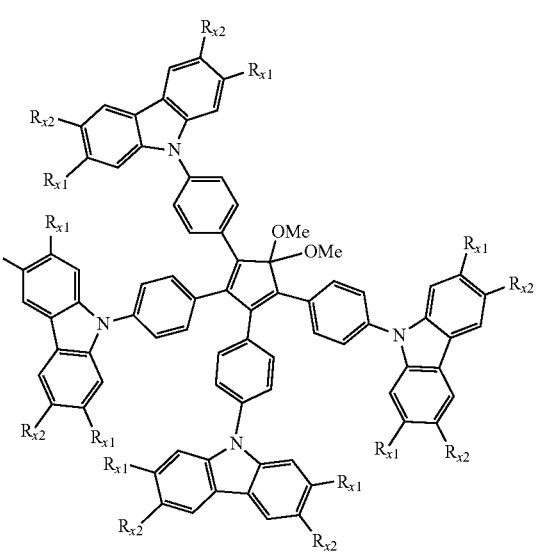

As a preferred embodiment, the invention provides a compound, 4,4',4'',4'''-(5,5-dimethoxycyclopenta-1,3-diene-1,2,3,4-tetrayl)tetrakis(N,N-bis(4-methoxyphenyl)aniline (CPDA 1), having the formula (A)

(A)

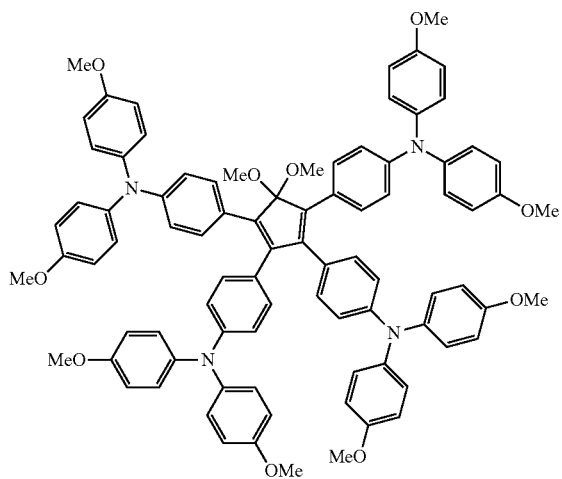

The invention thus provides CPDA 1, comprising cyclopentadiene dimethyl acetale as a new core element flanked by four triarylamine moieties as a novel HTM for PSCs. CPDA 1 surpasses spiro-OMeTAD in points mentioned above by a record PCE of 23.1% for non-Spiro PSC, substantially higher stability and low-cost.

Under another aspect, the invention proposes a process for synthetizing CPDA 1. This process comprises a step consisting in a fourfold Suzuki cross-coupling reaction starting from commercially available tetrabromocyclopentadiene dimethyl acetale and a triarylamine boronic ester.

On the other hand, dimethyl acetale can be efficiently prepared in two steps and the boronic ester in three steps according to literature procedures[12]. The complete elaborated synthetic procedure over six steps delivers CPDA 1 in good overall yields of 52% starting from industrial-level chemicals.

Further features and advantages of the invention will appear to those skilled in the art from the dependent claims and from the detailed description of preferred embodiments in relation with the appended drawings.

DETAILED DESCRIPTION OF THE INVENTION

Figure 1:
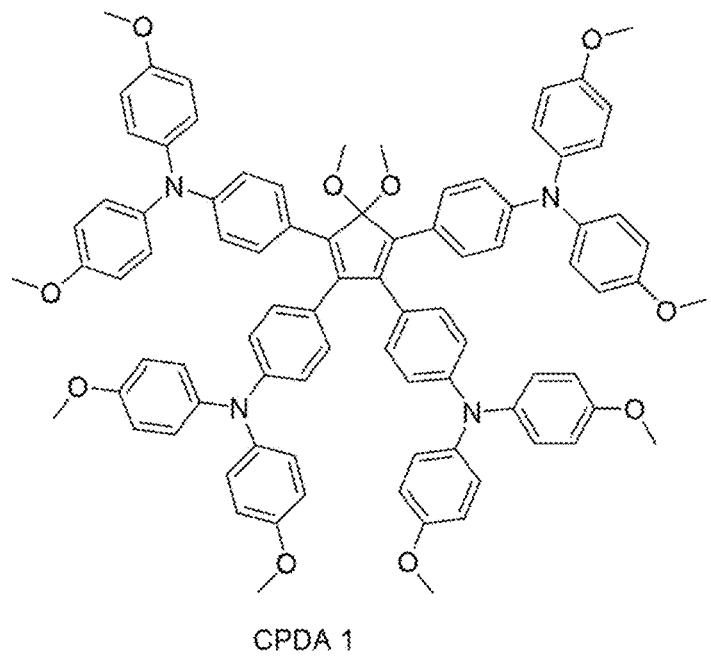
FIG. 1 shows the chemical structure of CPDA 1 and, in comparison the structure of the known compound Spiro-OMeTAD.
Figure 1:
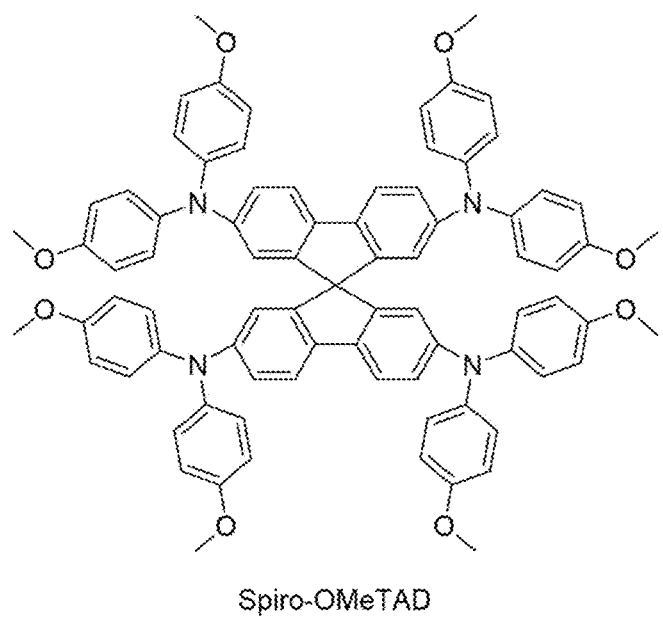

FIG. 1 shows the chemical structure of CPDA 1 and, in comparison the structure of the known compound Spiro-OMeTAD.

Figure 2:
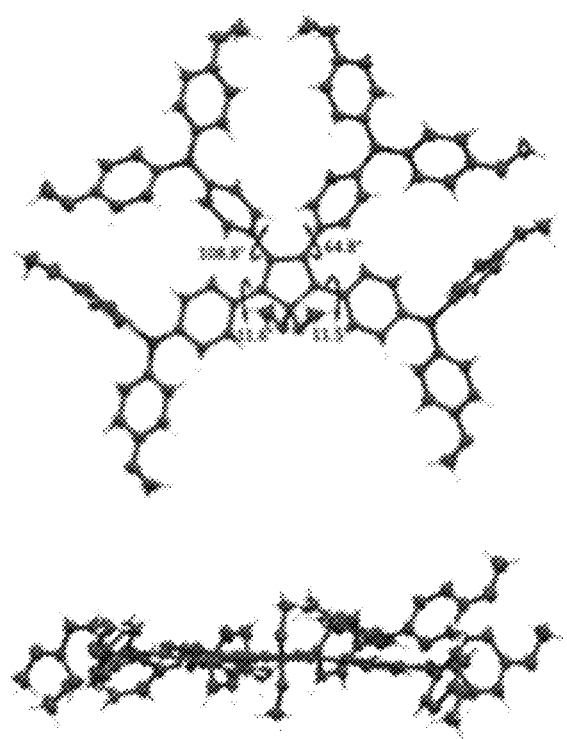
FIG. 2 shows a single crystal X-ray structure analysis of CPDA 1 in front (top) and side (bottom) view.

FIG. 2 shows a single crystal X-ray structure analysis of CPDA 1 showing the molecular geometry comprising torsion angles between the inner phenyl rings and the central cyclopentadiene dimethyl acetale core unit. Single crystals suitable for X-ray diffraction measurements were obtained by antisolvent vapor-assisted crystallization by slow diffusion of n-hexane into a dichloromethane solution of CPDA 1. In FIG. 2 the molecular geometry of CPDA 1 including torsion angles between the inner phenylene rings and the central cyclopentadiene dimethyl acetale core is shown in front and side view. The inner phenylene rings of the four triarylamine substituents attached at the 2,5-position of the CPDA unit showed rather small torsion angles of around 11.5° whereas the respective phenylenes at the 3,4-positions are strongly distorted from planarity by 65° and 109° (FIG. 2, top). As a consequence, the corresponding bond lengths are shorter for the 2,5-connection (1.464 Å and 1.458 Å) compared to the 3,4-substitution (1.481 Å and 1.479 Å) indicating a higher—pi-conjugation in this pathway. The spiro-carbon of the central CPDA unit is nearly ideally tetrahedral and the methoxy groups are only slightly distorted by 2-7° (FIG. 2, bottom). It is worth mentioning that the molecular packing motif of CPDA 1 in the (−101) plane is dominated by CH—O interactions of methoxy groups. In the perpendicular direction several CH—C and CH—O intermolecular interactions stabilize the antiparallel oriented molecules in the adjacent planes. The short contacts involving hydrogen atoms in herringbone-type interaction that is related to the packing tendency of CPDA 1 is supposed to favour better hopping conduction of holes in the HTL of PSC.

Figure 3:
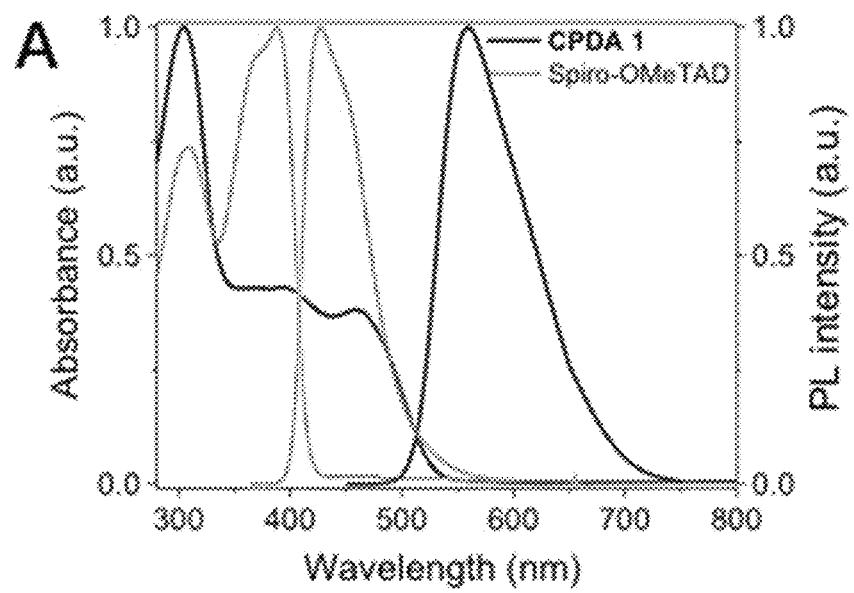
FIG. 3 shows UV-PL spectra of CPDA1 and Spiro-OMeTAD HTM films.

The optical properties of CPDA 1 by UV-Vis and fluorescence spectroscopy in dichloromethane solution are shown in FIG. 3. The absorption spectrum showed absorption maxima at $\lambda_1$=304 nm $\lambda_2$=396 nm $\lambda_3$=454 nm. Absorption spectrum of Spiro-OMeTAD is also shown as a comparison. The inventors assign the strongest high-energy absorption to the triarylamine chromophores in accordance with bis(4-methoxyphenyl)-amine, which shows an absorption maximum at 298 nm[13]. Another reasonable chromophore is represented by the 4,4'-bis(4-methoxyphenyl) stilbene unit, which as trans-isomer shows two absorption bands at 398 nm and 305 nm. It is known for cyclopentadienone acetales that in comparison to the corresponding cyclopentadienes the longest wavelength band is bathochromically shifted due to spiro-conjugation[15]. Therefore, the inventors address the band at lowest energy at 454 nm in the absorption spectrum of CPDA 1 to the spiro-conjugated cyclopentadiene acetale structure. The absorption onset corresponds to an optical energy gap of 2.37 eV and an emission maximum is found at 577 nm. The corresponding absorption maxima of thin films of CPDA 1 are not or only marginally red-shifted ($\lambda_1$=304 nm, $\lambda_2$=402 nm, $\lambda_3$=460 nm, $E_g$=2.30 eV) indicating rather amorphous character and low degree of aggregation. Such an amorphous behaviour endows CPDA 1 good film forming ability, which is potentially important to fabricate thin, yet confocal HTM layers for efficient PSCs.

Figure 4:
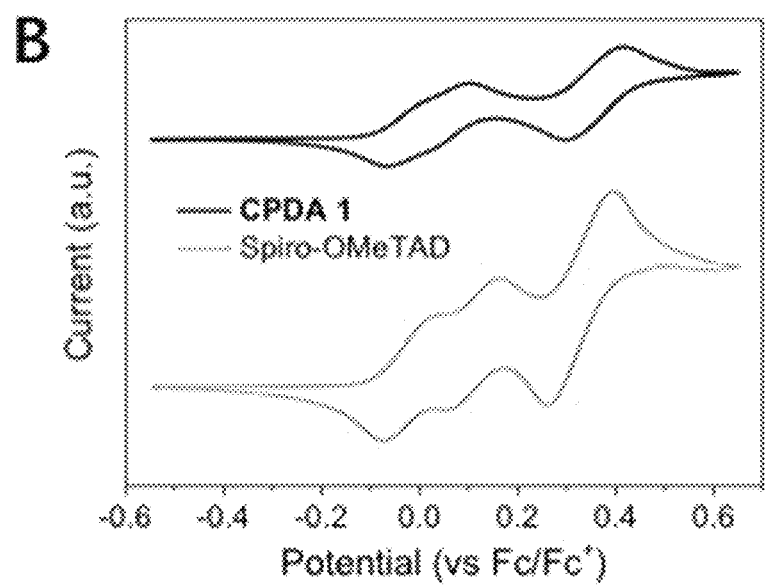
FIG. 4 shows cyclic voltammograms of CPDA1 and Spiro-OMeTAD.
Figure 5:
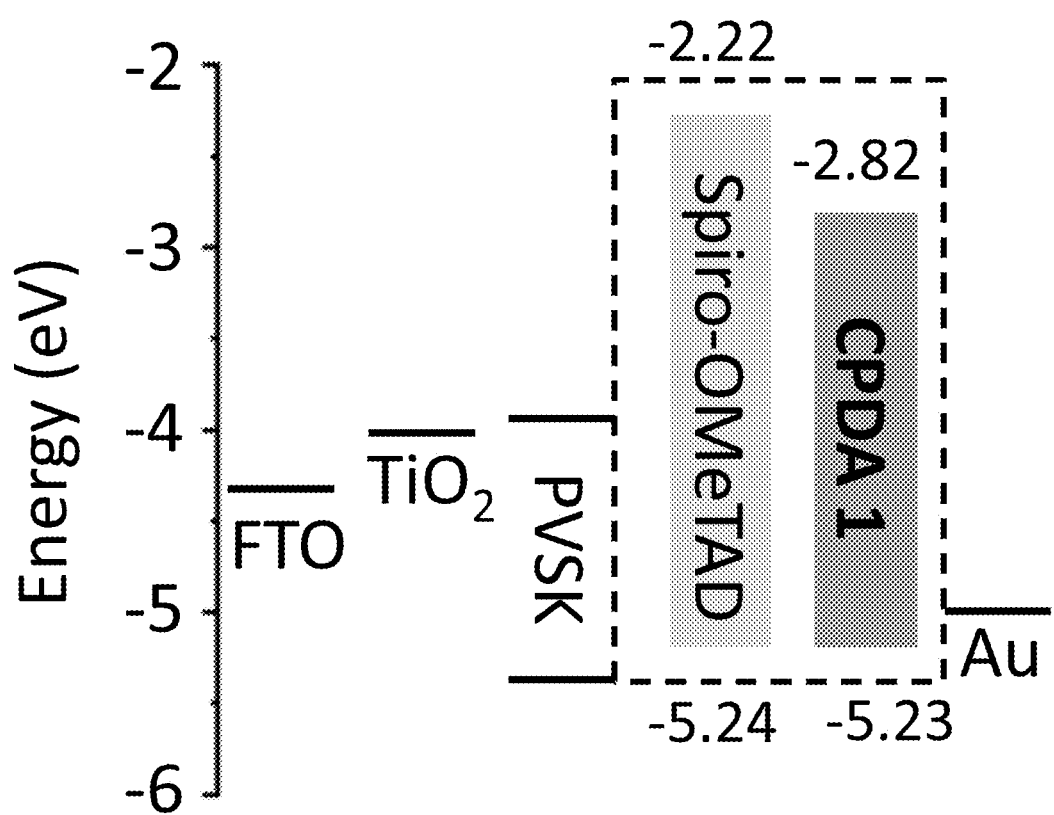
FIG. 5 is an energy level diagram of CPDA1 and Spiro-OMeTAD based devices, FIG. 6 show cross-section SEM photos of PSCs with CPDA1 (left) and Spiro-OMeTAD (right) as HTM, the scale bar representing 200 nm.

The cyclic voltammograms of CPDA 1 and Spiro-OMeTAD are shown in FIG. 4. Spiro-OMeTAD and CPDA 1 both exhibit three reversible redox peaks. CPDA 1 (black line) has to very close electron transfer occurring around 0 V vs. Fc/Fc$^+$ followed by a more distant reversible redox event around 0.3 V vs. Fc/Fc$^+$. Spiro-OMeTAD (grey line) also has two very closely located electron transfer around 0 V vs. Fc/Fc$^+$. The HOMO level of CPDA 1 was calculated to be −5.23 eV and −5.24 eV for Spiro-OMeTAD. The LUMO level of Spiro-OMeTAD and CPDA 1 was respectively found to be −2.22 and −2.82 eV upon combination of the HOMO level and the optical band gap. As the energy level diagram for device components shows in FIG. 5, the HOMO level of CPDA 1 is more positive than the valence band of the perovskite layer, which makes it suited for hole extraction from the HTM/perovskite interface. The LUMO level is lying high enough to prevent back-electron transfer from the cathodic electrode to the perovskite layer[16].

The performance of CPDA 1 in PSCs are verified firstly by time-resolved photoluminescence to obtain insights of hole-extraction and also compared with Spiro-OMeTAD. The decay lifetimes of pristine perovskite films, perovskite films coated with CPDA 1 and Spiro-OMeTAD were 104.7 ns, 31.1 ns and 42.3 ns, respectively. Both CPDA 1 and Spiro-OMeTAD can effectively extract holes generated from the excitation of perovskite, while CPDA 1 favours slightly faster hole extraction, which presumably favours higher fill factor for the corresponding PSCs[17].

Differential scanning calorimetry thermograms of CPDA 1 permit to determine $T_g$ to be 120° C., which is identical with that of spiro-MeOTAD[18]. Further heating indicated exothermic crystallization in the range of 170–205° C. (supported by optical microscopy), and finally a broad melting point peaking at 257° C. was identified. In order to investigate the phase transition behaviour and thermal stability of the operative photoactive layer in the solar cells, DSCs of CPDA 1 containing the additives lithium bis (trifluoromethanesulfonyl) imid (LiTFSI) and 4-tert-butylpyridine (4-tBP) were measured. Interestingly, $T_g$ (120-125° C.) and the melting point (257° C.) of CPDA 1 are only marginally influenced by the additives, while the $T_g$ of Spiro-OMeTAD with dopants dropped to ~70° C.[19], which is harmful for the PSCs at operational conditions. In addition, HTM CPDA 1 is thermally stable and decomposition, which is attended by the loss of a methoxy group, started at a temperature of 280° C. (95% mass loss) measured by thermal gravimetric analysis.

Example 1: Synthesis of CPDA 1

Materials

Cesium iodide (CsI) was purchased from TCI Co. Ltd. Lead iodide (PbI$_2$) was purchased from Alfa Co. Ltd. Formamidinium iodide (FAI), Methylammonium bromide (MABr), and 2,2',7,7'-Tetrakis [N,N-di(4-methoxyphenyl) amino]-9,9'-spirobifluorene (spiro-OMeTAD) were purchased from Dyesol. Ultradry dimethylformamide (DMF), ultradry dimethyl sulfoxide (DMSO) and ultradry chlorobenzene (CB) were purchased from Acros. lithium bistrifluorosulfonyl imide (Li-TFSI), acetyl acetone, phenethylamine and titanium diisopropoxide bis(acetylacetonate), 75 weight % in IPA were purchased from Sigma-Aldrich. All the chemicals were used as received without further purification.

Synthesis Procedures for the Preparation of CPDA 1 a) Synthesis of 1,2,3,4-tetrabromo-5,5-dimethoxycyclopentadiene according to reference 1:

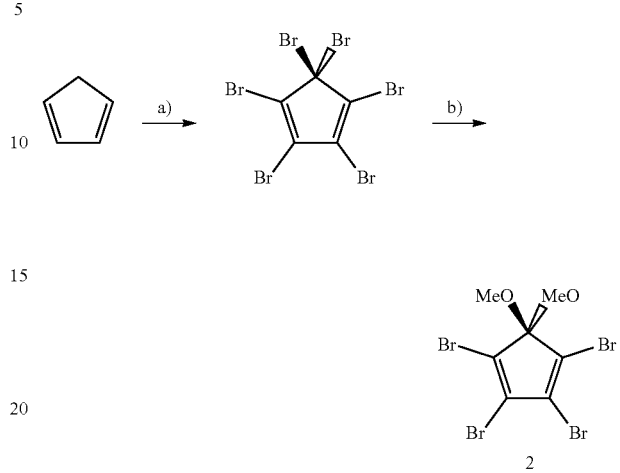

Scheme S1: a) KOBr, KOH, H$_2$O, −5° C., 44%. b) NaOMe, diglyme, −78° C., 93%[1].

b) Synthesis of 4-methoxy-N-(4-methoxyphenyl)-N-(4-(4,4,5,5-tetramethyl-1,3,2-dioxaborolan-2-yl)phenyl)aniline according to bibliographic references 2-4:

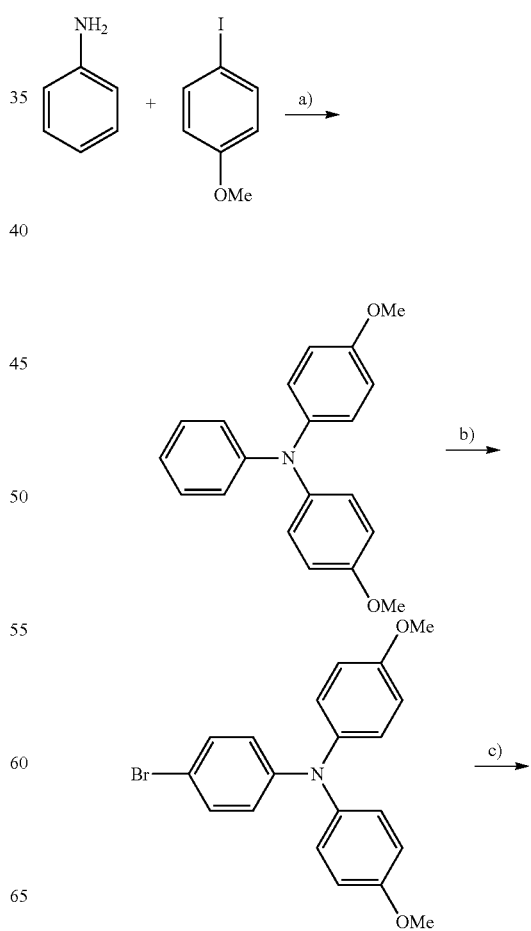

-continued

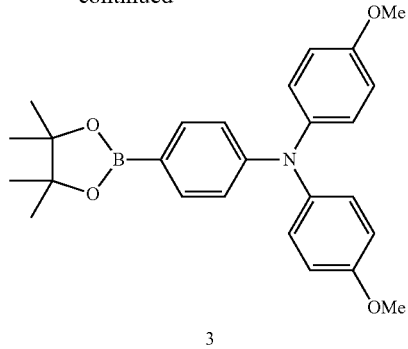

3

Scheme S2: a) Cut, 2,2'-bipyridin, KOtBu, PhMe, 115° C., 3.5 h, 95%[2]. b) NBS, THF, 0° C., 3 h, 91%[3]. c) Diborane pinacol ester, Pd(dppf)Cl$_2$.CH$_2$Cl$_2$, KOAc, DMF, 80° C., 12 h, 82%[4].

c) Synthesis of 4,4'4'',4'''-(5,5-dimethoxycyclopenta-1,3-diene-1,2,3,4-tetrayl)tetrakis(N,N-bis(4-methoxyphenyl)aniline), CPDA 1. A 2 M potassium phosphate solution was freshly prepared and degassed with argon for 2 h. Dry THF was degassed for 1 h with argon. 1,2,3,4-Tetrabromo-5,5-dimethoxycyclopenta-1,3-diene (50 mg, 113 µmol), 4-methoxy-N-(4-methoxyphenyl)-N-(4-(4,4,5,5-tetramethyl-1,3,2-dioxaborolan-2-yl)phenyl)aniline (195 mg, 452 µmol), tetrakis(triphenylphosphane)palladium(0) (20 mg, 17 µmol) were filled into a Schlenk-tube and were evacuated for 1 h. THF (3 ml) was added and the solution was degassed for 5 minutes. K$_3$PO$_4$ (850 µl 2 M, 1.70 mmol) was added and the solution was degassed for another minute. The Schlenk-tube was sealed and the solution was heated to 80° C. for 72 h. The reaction mixture was cooled to room temperature, water was added, and the organic phase was extracted with diethyl ether and dried with magnesium sulfate. The crude product was purified by flash column chromatography with silica gel which was deactivated by triethyl amine. An eluent mixture of petrol ether:diethyl ether (1:1) and 3% triethylamine was used which was later changed to petrol ether:diethyl ether:toluene (2:2:1). The product was precipitated from DCM/PE and CPDA 1 was isolated as an orange solid (112 mg, 84 µmol, 73.9%). Mp 266° C. (DSC); $^1$H NMR (400 MHz, CD$_2$Cl$_2$) δ 7.42-7.36 (m, 4H), 7.10-7.02 (m, 8H), 7.03-6.96 (m, 8H), 6.88-6.79 (m, 8H), 6.83-6.76 (m, 10H), 6.78-6.69 (m, 4H), 6.73-6.65 (m, 4H), 3.78 (s, 6H), 3.76 (s, 6H), 3.19 (s, 6H); $^{13}$C NMR (101 MHz, CD$_2$Cl$_2$) δ 156.71, 156.40, 148.08, 147.78, 144.02, 141.36, 141.02, 133.88, 130.87, 129.41, 128.94, 127.55, 126.91, 125.79, 120.54, 119.03, 115.49, 115.12, 115.10, 55.96, 55.94, 50.89; HR-FTICR-MALDI: m/z: calcd. for C$_{87}$H$_{78}$N$_4$O$_{10}$: 1338.57179; found: 1338.57156 [M+] (δm/m=0.12 ppm).

Based on usual prices of the afore mentioned reagents and on the labour involved by the above described synthesis and purification procedures, the fabrication costs of CPDA 1 may be roughly estimated to between about 4-10 CHF/g, whereas the cost of spiro-OMeTAD is of about 100 CHF/g.

Example 2: Preparation of a PSC Incorporating CPDA 1

Substrate Preparation

Conductive glass, FTO (10 ohms/sq), was purchased from Nippon Sheet Glass, and titanium dioxide paste (30 NR-D) was purchased from Dyesol. An etched fluorine doped tin oxide (FTO) conducting glass was consecutively cleaned using Hellmanex (2%, deionized water), acetone and ethanol by sonicating for 10-15 min for each solvent. Instead of fluorine-doped tin oxide (FTO), indium-doped tin oxide (ITO) and so on could be used. After drying with compressed air, the glass was further cleaned by UV-ozone for 15 min. Compact TiO$_2$ layer was deposited on top of FTO glass using the spray pyrolysis method (02 as the carrier gas): The substrate was preheated to 450° C.; a precursor solution was diluted 0.6 mL titaniumdiisopropoxide bis(acetylacetonate), 75 wt % in IPA and 0.4 mL acetyl acetone with 9 mL dry ethanol. After spray pyrolysis, the FTO/c-TiO$_2$ substrate was heat at 450° C. for 5 min before cooling down to ambient temperature. Next, mesoporous TiO$_2$ (m-TiO$_2$) layer was coated on the compact TiO$_2$ (c-TiO$_2$) substrate by spin-coating for 20 s at 4000 rpm with a ramp rate of 2000 rpm s$^{-1}$, using the commercial TiO$_2$ paste (30NRD, Dyesol) diluted with anhydrous ethanol at a weight ratio of 1:6. After drying at 80° C., the as-prepared FTO/c-TiO$_2$/TiO$_2$ paste was sintered at 450° C. for 30 min under dry air flow, yielding FTO/c-TiO$_2$/m-TiO$_2$, which was then deposited with perovskite freshly.

Perovskite Active Layer Deposition

Perovskite precursor solution was prepared by dissolving a mixture of PbI$_2$ (1.60 mmol, 735.3 mg), FAI (1.31 mmol, 224.4 mg), MABr (0.15 mmol, 16.2 mg), and CsI (0.08 mmol, 19.8 mg) Cs$_{0.05}$FA$_{0.85}$MA$_{0.10}$Pb(I$_{0.97}$Br$_{0.03}$)$_3$ with 5% excess of PbI$_2$ in 1 mL of mixed solution of DMF and DMSO [DMF (v):DMSO (v)=4:1] under mild heating condition at ~70° C. to assist dissolving. The perovskite active layer was deposited using an antisolvent method, with CB as the antisolvent. The perovskite precursor solution was deposited on the freshly prepared FTO/c-TiO$_2$/m-TiO$_2$ substrate, and a two-step spin-coating method was applied. The first step was carried out at 2000 rpm with an acceleration rate of 200 rpm/s for 10 s. The second step followed at 6000 rpm with an acceleration rate of 2000 rpm/s for 30 s. CB (100 µL) was slowly dripped at the 15 s before the second step end. After this, the substrate was annealed at 120° C. for 20 min. The preparation of the perovskite layer was carried out in a dry air-filled glove box with the relative humidity about 2%.

Hole-Transporting Layers

Comparative layer: Spiro-OMeTAD was dissolved in CB with a concentration of 77.6 mM, 1 mL Spiro-OMeTAD solution was doped by 20.6 µL Li-TFSI (520 mg/mL in Acetonitrile) and 35.5 µL t-BP. The mixed Spiro-OMeTAD solution was spin coated on the surface of the perovskite at 4000 rpm for 20 s with an acceleration rate of 2000 rpm/s.

CPDA 1 was dissolved in CB with a concentration of 15 mM; 1 mL CPDA 1 solution was doped by 2.5 µL Li-TFSI (520 mg/mL in Acetonitrile) and 6.6 µL tBP. The mixed CPDA1 solution was spin coated on the surface of the perovskite at 4000 rpm for 20 s with an acceleration rate of 2000 rpm/s.

Gold Electrode

The gold electrode was thermally evaporated on the surface of the Spiro-OMeTAD, respectively CPDA 1, with the shadow mask with an aperture area of 5 mm by 5 mm. The thickness of the gold electrode was adjusted to 80 nm, and the evaporation speed was adjusted to 0.01 nm s−1 at the first 10 nm, 0.02 nm s−1 for the thickness between 10 nm and nm and 0.08 nm s$^{-1}$ for the rest 60 nm.

Figure 6:
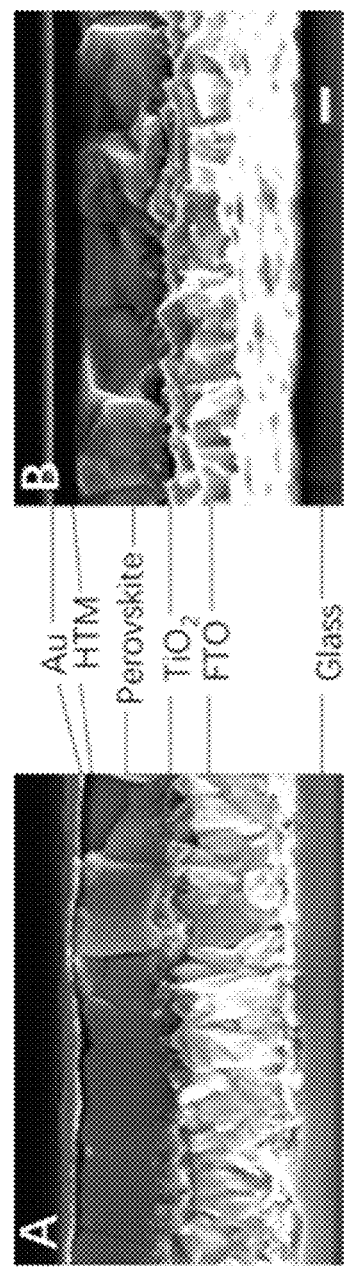

The structures obtained are illustrated by the cross-section SEM photos of FIG. 6. To note that in the left PSC, comprising CPDA 1 as HTM, the CPDA 1 HTM layer is thinner than the Spiro-OMeTAD layer of the PSC at the right. Thus the inventive PSC needs less HTM.

Example 3: Photovoltaic Performance Measurements

To investigate the application of CPDA 1 in solar cells, PSCs are fabricated with a standard structure of Glass/FTO/compact-$TiO_2$/mesoscopic-$TiO_2$/perovskite/HTM/gold as disclosed in example 2 hereabove.

Current-voltage characteristics were recorded under ambient temperature and air conditions. The PSCs were measured using a 300-W Xenon light source from Oriel. The spectral mismatch between AM 1.5G and the solar simulator was calibrated by a Schott K113 Tempax filter (Prazosopms Glas & Optik GmbH). A silicon photodiode was used as light intensity calibrator for each measurement. Keithley 2400 was used for the current-voltage scan by applying an external voltage bias and measuring the response current with a scan rate of 50 mV/s. The cells were masked with a black metal mask with an area of 0.16 $cm^2$. IPCE was recorded with a commercial apparatus (Aekeo-Ariadne, Cicci Research s.r.l.) based on a 300-W Xenon lamp. Operational stability of the cells was measured under a white light-emitting diode lamp with biologic MPG2 potentiostat and was performed under $N_2$ gas flow. The device area was masked to around 0.16 $cm^2$. The spectral mismatch between AM 1.5G and the solar simulator was calibrated by a Schott K113 Tempax filter, whose light intensity was calibrated with a silicon diode. The light intensity was around 83 mW $cm^{-2}$, and the actual current was adjusted according to in-time calibration result from the silicon diode. The ambient stability data were acquired from the tracking of a unencapsulated device exposed to open air. The relative humidity of the ambient atmosphere varies from 40-60%. Relative humidity was monitored by Sigma-Aldrich Humidity/Temperature Pen 445580.

Figure 7:
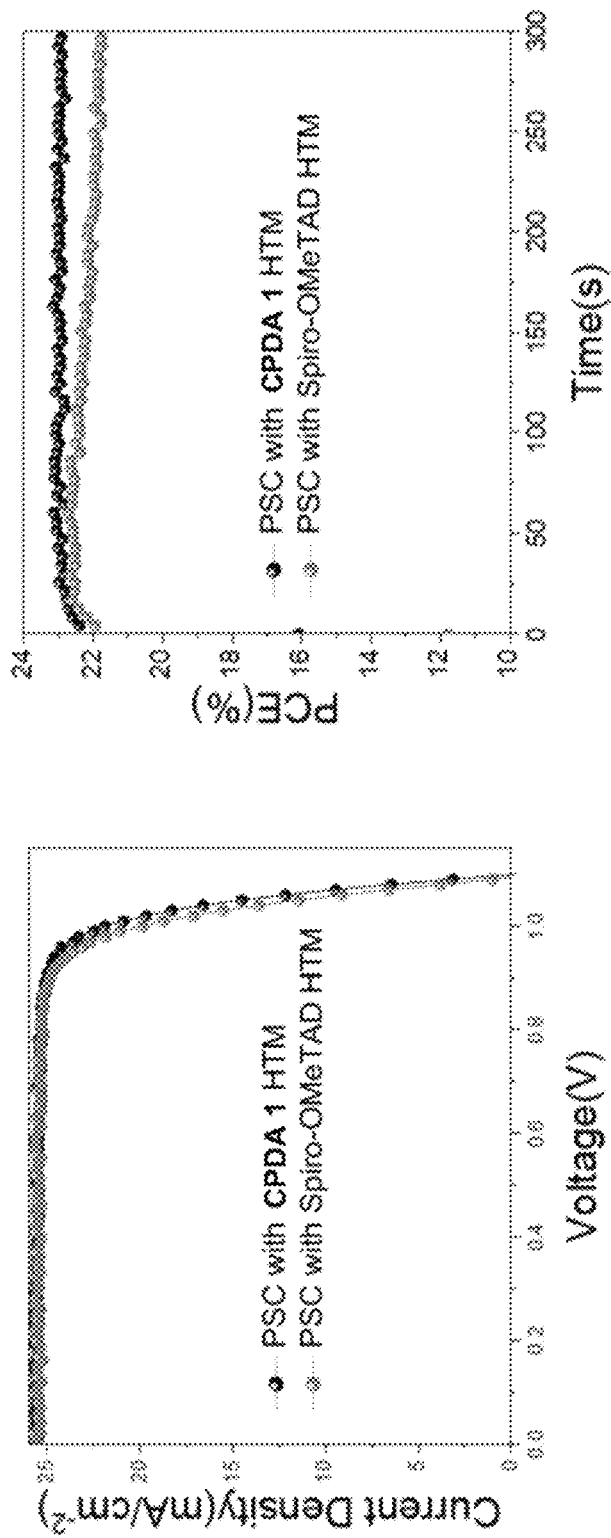
FIG. 7 shows I-V curves of PSCs with CPDA1 and Spiro-OMeTAD, FIG. 8 (A, C, D) shows ageing effects under operating conditions of PSCs with CPDA1 and Spiro-OMeTAD respectively, and B is images of water droplets on the surface of perovskite film coated with Spiro-OMeTAD (top) and CPDA 1 (bottom)
Figure 9:
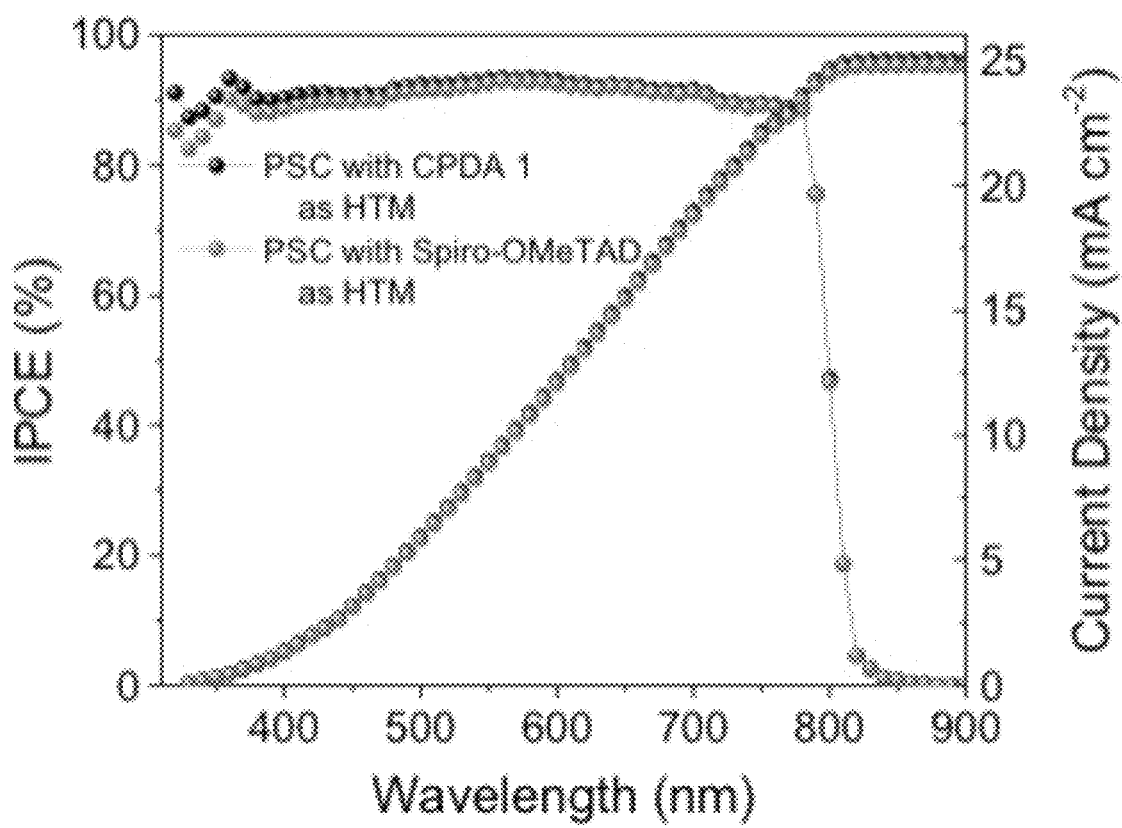
FIG. 9 shows IPCE curves and integrated photocurrent of PSCs with CPDA 1 and Spiro-OMeTAD HTMs.

The current density-voltage (J-V) curves of devices based on CPDA 1 (black curve) and Spiro-OMeTAD (grey curve), measured under AM 1.5G irradiation are displayed in FIG. 7 and the corresponding photovoltaic parameters summarized in Table 1. A representative cell with a PCE of 23.1% was fabricated using CPDA 1 as HTM. This device produced a $V_{OC}$ of 1099 mV, a fill factor (FF) of 82.1% and a $J_{SC}$ of 25.6 mA $cm^{-2}$. PSCs based Spiro-OMeTAD, fabricated under the same condition for reference, obtained a slightly lower PCE of 22.6%. The CPDA 1 based device was scanned in both reverse (RVS) and forward (FWS) way and the obtained PV parameters showed less hysteresis compared to PSC with Spiro-OMeTAD as HTM. The observed slight outperformance of CPDA 1 based PSC is in agreement with the aforementioned results together with reduced HTL thickness for CPDA 1. The stabilized power output at the maximum power point (MPP) stability of champion PSCs with CPDA 1 and Spiro-OMeTAD HTMs were monitored under dehumidified ambient air (10% RH). Within the first 5 min, CPDA 1 based PSC presents a stable power output of 22.98% (see inset of FIG. 7), which is approaching the PCE obtained from backward J-V scan. However, the output PCE of Spiro-OMeTAD HTM based PSC decrease from 22.50% to 21.87%, implying better operational stability of device based on CPDA 1 HTM. The incident photon-to-current conversion efficiencies (IPCE) of the champion devices based on CPDA 1 and Spiro-OMeTAD are shown in FIG. 9. The integrated photocurrents are in good agreement with the corresponding $J_{SC}$ values measured from J-V curves (Table 1).

TABLE 1

PV parameters of PSCs

| HTM in PSC | $V_{OC}$ | $J_{SC}$[c] [mA/$cm^2$] | $J_{SC}$[d] [mA/$cm^2$] | FF [%] | PCE[e] [%] | PCE[f] [%] |
|---|---|---|---|---|---|---|
| CPDA 1 RVS[a] | 1.099 | 25.60 | 24.98 | 0.821 | 23.10 | 22.98 |
| CPDA 1 FWS[b] | 1.093 | 25.61 | | 0.816 | 22.84 | |
| Spiro-OMeTAD RVS | 1.091 | 25.54 | 24.78 | 0.810 | 22.57 | 21.87 |
| Spiro-OMeTAD FWS | 1.081 | 25.56 | | 0.805 | 22.24 | |

[a] reverse scan;
[b] forward scan;
[c] $J_{SC}$ determined from the IV measurement;
[d] JSC determined from IPCE;
[e] PCE determined from the IV measurement;
[f] PCE determined from 300 s MPP tracking.

Figure 8:
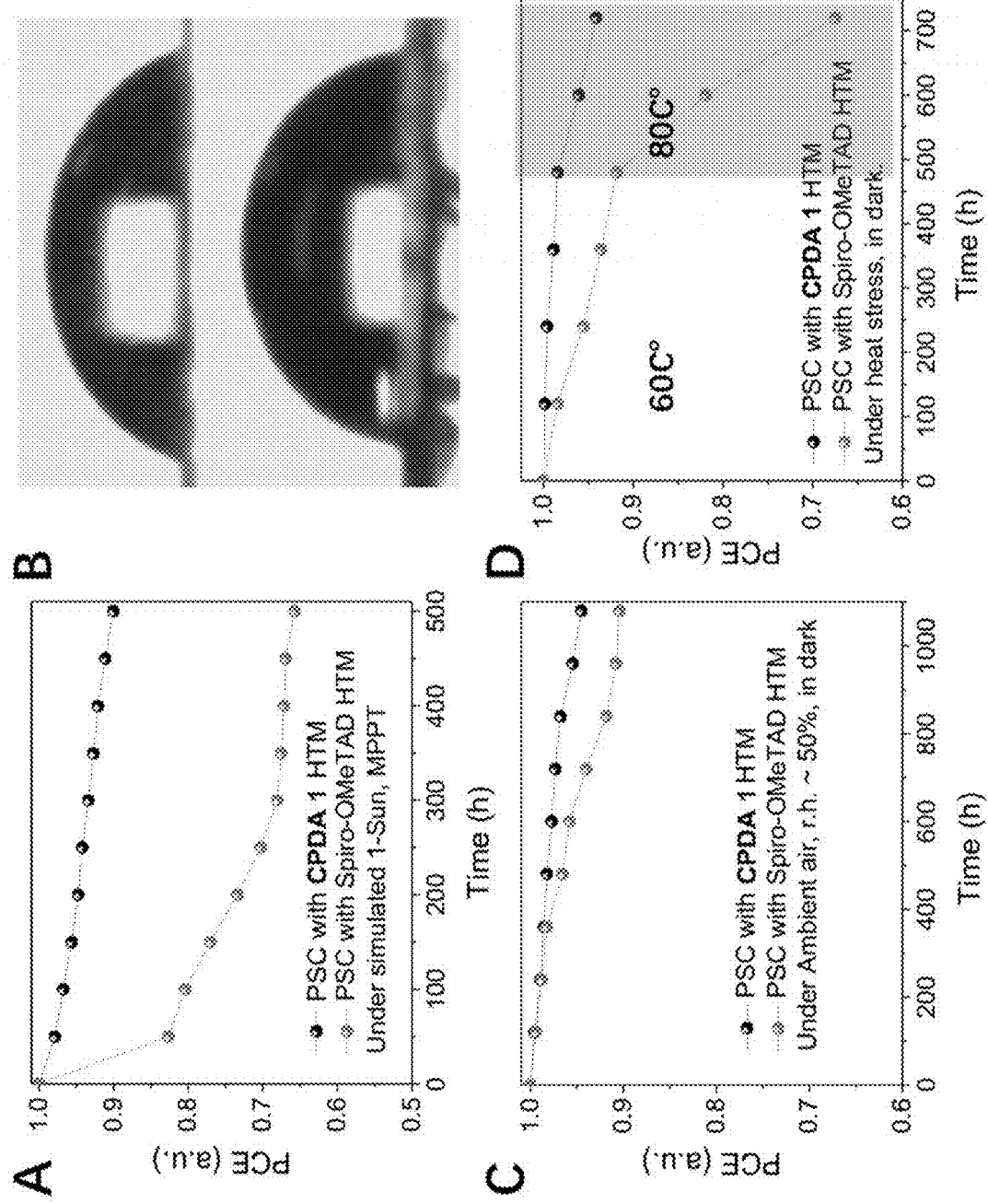

Operational stability devices based on CPDA 1 and Spiro-OMeTAD without encapsulation was performed under 1 sun irradiation and under nitrogen atmosphere ($N_2$). The results are shown in FIG. 8A. After 500 hours, the device based on CPDA 1 HTM retained 90% of its initial efficiency, in contrast to 65% for the one with Spiro-OMeTAD. In addition, fast decay within the first 50 h up to 18% (burn-in) was observed, in agreement of the stable power output measurement as shown in FIG. 7. CPDA 1 HTM based PSCs exhibit superior operational stability as compared to Spiro-OMeTAD, which is of great importance for industrial application for the advanced PSC technique. Due to the reduced hydrophilic dopant Lithium bis(trifluoromethanesulfonyl) imide (LiTFSI) and tert-butyl pyridine (t-BP) that is introduced into CPDA 1 HTL, one observes better resistivity of CPDA 1 based PSCs as compared to Spiro-OMeTAD.

Contact angle measurement were performed for perovskite film coated with CPDA 1 or Spiro-OMeTAD HTL, and the results are shown in FIG. 8B: FIG. 8B shows images of water droplets on the surface of the respective perovskite films. An increased contact angle from 85.1° to 69.6° for CPDA 1 based sample as compared to Spiro-OMeTAD was observed.

The stability of the PSCs based on both HTMs stored in ambient atmosphere with an RH (relative humidity) of 40-60%, were monitored and the results are shown in FIG. 8C. The better stability for PSC based on CPDA 1 may be attributed to less moisture uptake that is related to minor amount of hydrophilic dopant.

PSCs based on Spiro-OMeTAD HTL generally exhibit poor stability under heat stress due to the lowered $T_g$ after doping. FIG. 8C shows that at an ageing temperature of 60° C., both PSC exhibit good stability, that after 470 h CPDA 1 PSC showed no decay and Spiro-OMeTAD less than 10%. While at elevated temperature of 80° C., Spiro-OMeTAD based PSC dropped significantly by ~30% within 250 h, in contrast to −10% for PSC with CPDA 1 HTM. Due to the low $T_g$ of Spiro-OMeTAD (<80° C.), the Spiro-OMeTAD HTL suffered from film deformation that is related to glass transition, while the high $T_g$ of CPDA 1 HTL of 120° C. assured minor degradation by forming a robust film against heat stress.

In conclusion, the new organic small molecule HTM herein named CPDA 1 shows electrochemical properties very close to spiro-OMeTAD indicating a high compatibility with PSC systems. The implementation of the CPD core helped to red shift the absorption onset of the films as well as provide a flexible spatial configuration of the molecule, which is essential for optimum film forming properties. Transient and steady state emission analysis as well as hole mobility measurements indicate that the new HTM allows a better charge extraction, transport and separation than the spiro-OMeTAD reference compound. PSCs based on the new CPDA 1 show an impressive PCE close to 23% with lower hysteresis than its analogue. Stability studies performed under ambient, heated and humid conditions all showed that CPDA 1 is over performing spiro-OMeTAD. Furthermore the production cost of CPDA 1 is about 10 times lower than that of spiro-OMeTAD, contributing to render PSCs more affordable.

BIBLIOGRAPHICAL REFERENCES

[1] a) Y. Wang, T. Wu, J. Barbaud, W. Kong, D. Cui, H. Chen, X. Yang, L. Han, X. Yang, L. Han, L. Han, Science 2019, 365, 687; b) E. H. Jung, N. J. Jeon, E. Y Park, C. S. Moon, T.-Y. Yang, J. H. Noh, J. Seo, C. S. Moon, J. H. Noh, T. J. Shin, Nature 2019, 567, 511; c) S. Bai, P. Da, C. Li, Z. Wang, Z. Yuan, F. Fu, M. Kawecki, X. Liu, N. Sakai, J. T.-W. Wang, S. Huettner, S. Buecheler, M. Fahlman, F. Gao, H. J. Snaith, Nature 2019, 571, 245; d) H. Zhu, Y Liu, F. T. Eickemeyer, L. Pan, D. Ren, M. A. Ruiz-Preciado, B. Carlsen, B. Yang, X. Dong, Z. Wang, H. Liu, S. Wang, S. M. Zakeeruddin, A. Hagfeldt, M. I. Dar, X. Li, M. Grätzel, Advanced Materials, n/a, 1907757.
[2] NREL, National Renewable Energy Laboratory, https://www.nrel.gov/pv/cell-efficiency_html, 2019.
[3] a) Y. Li, K. R. Scheel, R. G. Clevenger, W. Shou, H. Pan, K. V. Kilway, Z. Peng, Adv. Energy Mater 2018, Ahead of Print; b) C. Lu, I. T. Choi, J. Kim, H. K. Kim, J. Mater. Chem. A 2017, Ahead of Print.
[4] a) X. Liu, F. Zhang, Z. Liu, Y Xiao, S. Wang, X. Li, Journal of Materials Chemistry C 2017, 5, 11429; b) W. Yu, Q. Yang, J. Zhang, D. Tu, X. Wang, X. Liu, G Li, X. Guo, C. Li, ACS Appl Mater Interfaces 2019; c) H. D. Pham, T. T. Do, J. Kim, C. Charbonneau, S. Manzhos, K. Feron, W. C. Tsoi, J. R. Durrant, S. M. Jain, P. Sonar, Adv. Energy Mater. 2018, Ahead of Print.
[5] P. M. Sonar, H. D. Pham, K. Kazumasa Hayasaka, H. Matsui, S. Tokito, J. Kim, S. M. Jain, J. Durrant, W. Tsoi, T. M. Watson, N. Motta, T. T. Do, K. Feron, S. Manzhos, J. Mater. Chem. C 2017, Ahead of Print.
[6] a) K. Guo, M. Wu, S. Yang, Z. Wang, J. Li, X. Liang, F. Zhang, Z. Liu, Z. Wang, Sol. RRL 2019, 3, n/a; b) C. Yin, J. Lu, Y Xu, Y Yun, K. Wang, J. Li, L. Jiang, J. Sun, A. D. Scully, F. Huang, J. Zhong, J. Wang, Y-B. Cheng, T. Qin, W. Huang, Adv. Energy Mater 2018, Ahead of Print.
[7] a) S. S. Reddy, K. Gunasekar, J. H. Heo, S. H. Im, C. S. Kim, D. H. Kim, J. H. Moon, J. Y Lee, M. Song, S. H. Jin, Advanced Materials 2016, 28, 686; b) T. H. Schloemer, T. S. Gehan, J. A. Christians, D. G Mitchell, A. Dixon, Z. Li, K. Zhu, J. J. Berry, J. M. Luther, A. Sellinger, ACS Energy Lett. 2019, Ahead of Print.
[8] H. Min, M. Kim, S.-U. Lee, H. Kim, G Kim, K. Choi, J. H. Lee, S. I. Seok, Science 2019, 366, 749.
[9] S. Daskeviciute, N. Sakai, M. Franckevicius, M. Daskeviciene, A. Magomedov, V. Jankauskas, H. J. Snaith, V. Getautis, Adv. Sci. (Weinheim, Ger) 2018, 5, n/a.
[10] T. Malinauskas, D. Tomkute-Luksiene, R. Sens, M. Daskeviciene, R. Send, H. Wonneberger, V. Jankauskas, I. Bruder, V. Getautis, ACS Applied Materials & Interfaces 2015, 7, 11107.
[11] a) D. Li, Y Li, Y Li, Q. Meng, J.-Y. Shao, L.-Y. Deng, Y-W. Zhong, Chem Commun (Camb) 2018, 54, 1651; b) F. Zhang, S. Wang, H. Zhu, X. Liu, H. Liu, X. Li, Y. Xiao, S. M. Zakeeruddin, M. Gratzel, ACS Energy Lett. 2018, Ahead of Print; c) R. Grisorio, B. Roose, S. Colella, A. Listorti, G P. Suranna, A. Abate, ACS Energy Lett. 2017, Ahead of Print; d) F. Zhang, C. Yi, P. Wei, X. Bi, J. Luo, G Jacopin, S. Wang, X. Li, Y. Xiao, S. M. Zakeeruddin, M. Grätzel, Advanced Energy Materials 2016, n/a; e) Z. a. Li, Z. Zhu, C.-C. Chueh, J. Luo, A. K. Y. Jen, Advanced Energy Materials 2016, 6, 1601165; f) W. Zhu, C. Shen, Y Wu, H. Zhang, E. Li, W. Zhang, X. Xu, W. Wu, H. Tian, Angew Chem Int Ed Engl 2019; g) P. M. Sonar, H. D. Pham, S. M. Jain, L. Meng, S. Manzhos, K. Feron, S. Pitchaimuthu, Z. Liu, N. Motta, H. Wang, J. Durrant, J. Mater. Chem. A 2019, Ahead of Print; h) M. Saliba, S. Orlandi, T. Matsui, S. Aghazada, M. Cavazzini, J.-P. Correa-Baena, P. Gao, R. Scopelliti, E. Mosconi, K.-H. Dahmen, F. De Angelis, A. Abate, A. Hagfeldt, G Pozzi, M. Graetzel, M. K. Nazeeruddin, Nature Energy 2016, 1, 15017.
[12] a) A. Mahendran, P. Gopinath, R. Breslow, Tetrahedron Letters 2015, 56, 4833; b) A. A. Kelkar, N. M. Patil, R. V. Chaudhari, Tetrahedron Letters 2002, 43, 7143; c) K. Rakstys, A. Abate, M. I. Dar, P. Gao, V. Jankauskas, G Jacopin, E. Kamarauskas, S. Kazim, S. Ahmad, M. Grätzel, M. K. Nazeeruddin, Journal of the American Chemical Society 2015, 137, 16172; d) L. Chen, B. Zhang, Y Cheng, Z. Xie, L. Wang, X. Jing, F. Wang, Advanced Functional Materials 2010, 20, 3143.
[13] H. Li, C. Lambert, Chemistry—A European Journal 2006, 12, 1144.
[14] S. Barlow, C. Risko, S.-J. Chung, N. M. Tucker, V. Coropceanu, S. C. Jones, Z. Levi, J.-L. Brédas, S. R. Marder, Journal of the American Chemical Society 2005, 127, 16900.
[15] a) W. Lilienblum, R. W. Hoffmann, Chemische Berichte 1977, 110, 3405; b) H. Dürr, R. Gleiter, Angewandte Chemie International Edition in English 1978, 17, 559.
[16] J. Wu, C. Liu, H. Hu, X. Deng, W. Tan, Y Tian, B. Xu, J. Mater. Chem. A 2018, Ahead of Print.
[17] F. Qi, X. Deng, X. Wu, L. Huo, Y. Xiao, X. Lu, Z. Zhu, A. K. Y Jen, Adv. Energy Mater 2019, 9, 1902600 pp.
[18] U. Bach, D. Lupo, P. Comte, J. E. Moser, F. Weissortel, J. Salbeck, H. Spreitzer, M. Gratzel, Nature 1998, 395, 583.
[19] N. J. Jeon, H. Na, E. H. Jung, T.-Y. Yang, Y G Lee, G Kim, H.-W. Shin, S. Il Seok, J. Lee, J. Seo, Nat. Energy 2018, Ahead of Print.

The invention claimed is:

1. A compound having a structure comprising a substituted cyclopentadiene core flanked by four arylamine based moieties, having one of the formulas (I) and (II),

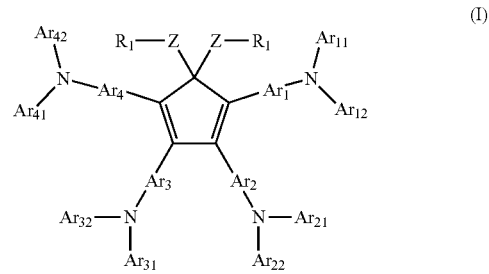

-continued

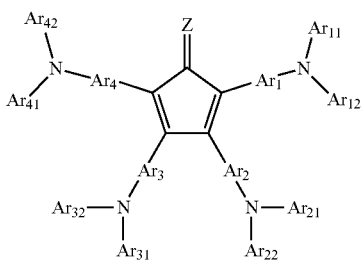
(II)

wherein Z=—CH$_2$—, or O or S or Se;
wherein R$_1$ is selected from C1-C20 linear or branched alkyl chains or alkoxy chains of formula

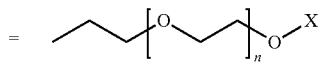

where X=(CH$_2$)$_n$NR$_x^{3+}$M$^-$; PR$_x^{3+}$M$^-$; SO$_3$R$_x$,
where R$_x$ is selected from C1-C20 linear or branched alkyl chains,
where M$^-$ represents a counterion, and
where n=0 to 20;
wherein Ar$_1$, Ar$_2$, Ar$_3$ and Ar$_4$ are identical or different moieties selected from aromatic or heteroaromatic ring systems having one or more aromatic rings comprising 5 to 40 ring atoms and one or more of the atoms or groups independently selected from C, N, O, S, Se, SiR'$_2$, or NR' wherein R' is selected from C1-C20 alkyl, C2-C20 alkenyl, C2-C20 alkynyl, C4-C20 unsubstituted and substituted aryl, and C1-C20 fluoroalkyl group, wherein said alkyl, alkenyl, alkynyl, and fluoroalkyl, if they comprise 3 or more carbons may be linear, branched or cyclic; and
wherein Ar$_{n1}$-Ar$_{n2}$ (with n=1, 2, 3, or 4) are identical or different moieties selected from aromatic or heteroaromatic ring systems having one or more aromatic rings comprising 5 to 40 ring atoms and one or more of the atoms or groups independently selected from C, N, O, S, Se, SiR'2, or NR', wherein R' is selected from C1-C20 alkyl, C2-C20 alkenyl, C2-C20 alkynyl, C4-C20 unsubstituted and substituted aryl, and C1-C20 fluoroalkyl group, wherein said alkyl, alkenyl, alkynyl, and fluoroalkyl, if they comprise 3 or more carbons may be linear, branched or cyclic.

2. A compound as claimed in claim 1, wherein said one or more aromatic rings is further substituted by one or more moieties independently selected from H, keto (=O) group, fluoro group, C1-C20 alkyl, C1-C20 alkoxy, C2-C20 alkenyl and C2-C20 alkynyl group.

3. A compound as claimed in claim 1, wherein Ar$_1$, Ar$_2$, Ar$_3$ or Ar$_4$ are identically or independently one from the other selected from the group consisting of

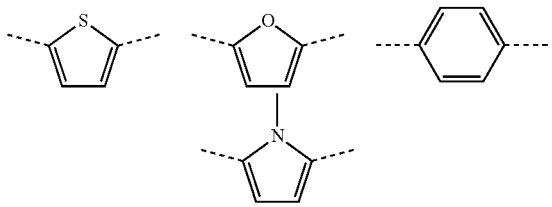

4. A compound as claimed in claim 1, wherein said aromatic ring may further be substituted by one or more moieties independently selected from H, keto (=O) group, fluoro group, C1-C20 alkyl, C1-C20 alkoxy, C2-C20 alkenyl and C2-C20 alkynyl group.

5. A compound as claimed in claim 1, wherein Ar$_{n1}$-Ar$_{n2}$ (n=1, 2, 3, 4) are, identically or independently one from the other, selected from

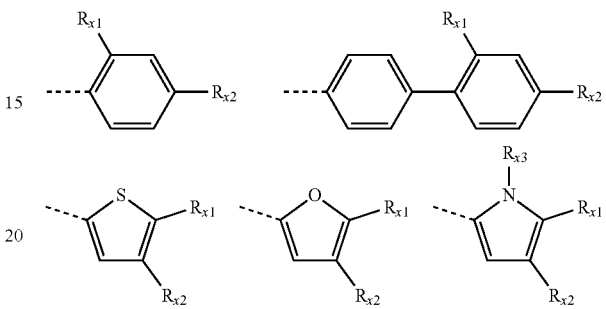

where R$_{x1}$ or R$_{x2}$ are selected from —H, —OR$_{x3}$, —SR$_{X3}$, —R$_{X3}$; and where R$_{x3}$ is selected from C1-C20 linear or branched alkyl chains or alkoxy chains;

or selected from

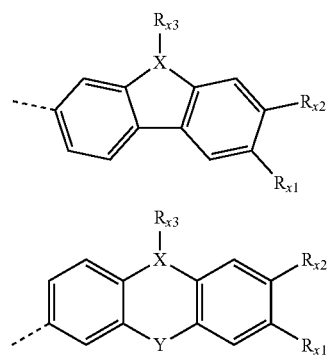

where R$_{x1}$ or R$_{x2}$ are selected from —H, —OR$_{x3}$, —SR$_{X3}$, —R$_{X3}$;
where X=N or P, where Y=O or S, and where R$_{x3}$ is selected from C1-C20 linear or branched alkyl chains, alkoxy chains;

or selected from

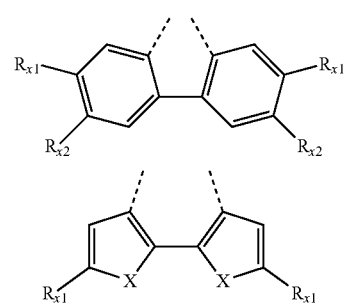

-continued

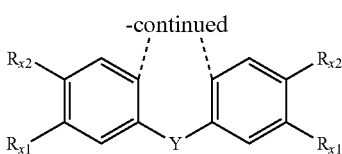

where $R_{x1}$ or $R_{x2}$ are selected from —H, —$OR_{x3}$, —$SR_{X3}$, —$R_{X3}$;

where X=N or P, where Y=O or S;

where $R_{x3}$ is selected from C1-C20 linear or branched alkyl chains, alkoxy chains; and where the two dashed-lines are prone to represent C—N bond that is connected to the central N atom in the arylamine moiety.

6. A compound as claimed in claim 1, wherein said counterion is selected from F⁻, I⁻, Br⁻, Cl⁻, [N(CN)$_2$]⁻, [N(SO$_2$CF$_3$)$_2$]⁻, [PF$_6$]⁻, [BF$_4$]⁻, [NO$_3$]⁻, [C(CN)$_3$]⁻, [B(CN)$_4$]⁻, [CF$_3$COO]⁻, or [ClO$_4$]⁻.

7. A compound as claimed in claim 1, wherein said compound is 4,4',4'',4'''-(5,5-dimethoxycyclopenta-1,3-diene-1,2,3,4-tetrayl)tetrakis(N,N-bis(4-methoxy-phenyl)aniline (CPDA 1), having the formula (A)

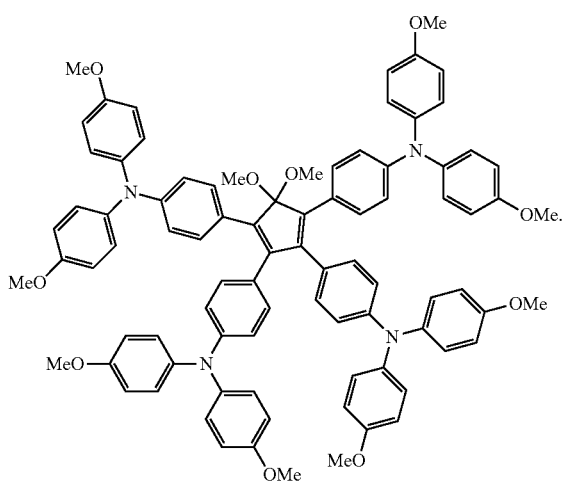

(A)

8. A process for synthetizing a compound as claimed in claim 1, comprising a step consisting in a fourfold Suzuki cross-coupling reaction, reacting a tetrabromocyclopentadiene dimethyl acetale and a triarylamine boronic ester.

9. A process for synthesizing the compound of claim 7, comprising steps consisting in a fourfold Suzuki cross-coupling reaction of:
   reacting a tetrabromocyclopentadiene dimethyl acetale and a triarylamine boronic ester; and
   reacting 1,2,3,4-tetrabromo-5,5-dimethoxycyclopenta-1,3-diene and 4-methoxy-N-(4-methoxyphenyl)-N-(4-(4,4,5,5-tetramethyl-1,3, 2-dioxaborolan-2-yl)phenyl)aniline in the presence of tetrakis(triphenylphosphane) palladium.

10. A solid state solar cell, comprising:
   a glass substrate surface coated with transparent metal oxide,
   a semi-conducting metal oxide layer deposited on top of said glass substrate with transparent metal oxide layer, forming a transparent/semiconductive metal oxide substrate,
   a perovskite photo-absorption layer deposited on the transparent/semiconductive metal oxide substrate,
   a hole transport material (HTM) layer deposited on the surface of the perovskite layer, and
   a counter-electrode,
   wherein said hole transport material (HTM) layer comprises a compound as claimed in claim 1.

11. A solid state solar cell as claimed in claim 10, wherein said hole transport material (HTM) layer further comprises a dopant.

12. A solid state solar cell as claimed in claim 10, wherein said dopant is lithium bis(trifluoromethanesulfonyl)imide (Li-TFSI) or zinc bis(trifluoromethanesulfonyl)imide (Zn(TFSI)$_2$).

13. A solid state solar cell as claimed in claim 10, wherein said metal oxide layer comprises a compact c-TiO$_2$ layer deposited on top of said FTO glass layer, and a mesoporous m-TiO$_2$ layer coated on the compact TiO$_2$ layer, forming a FTO/c-TiO$_2$/m-TiO$_2$ substrate.

* * * * *